US005382528A

United States Patent [19]

Scoville

[11] Patent Number: 5,382,528

[45] Date of Patent: Jan. 17, 1995

[54] METHOD OF USING A DISPOSABLE TAMPER EVIDENT LOCKING DEVICE

[75] Inventor: John R. Scoville, Henrietta, N.Y.

[73] Assignee: SPS Medical Supply Corporation, W. Henrietta, N.Y.

[21] Appl. No.: 16,092

[22] Filed: Feb. 10, 1993

Related U.S. Application Data

[63] Continuation of Ser. No. 598,946, Oct. 17, 1990, Pat. No. 5,225,162.

[51] Int. Cl.$^{6}$ .......... G01N 31/00; B31B 1/90

[52] U.S. Cl. .......... 436/1; 292/307 A; 422/119; 422/300; 422/310; 493/375

[58] Field of Search .......... 24/30.5 R, 30.5 P, 67 AR; 40/1.5, 1.6, 5, 6, 299, 330, 628, 630, 638, 645, 663, 664; 156/DIG. 5, DIG. 23; 206/439, 807; 220/214; 229/74, 76, 80, 80.5, 82, 102, 118, 123.2, 123.3; 283/74, 79-81, 97, 114, 900; 292/307 A; 422/26, 56, 119, 300, 310; 428/40, 41, 80, 124, 131, 136, 138, 537.5, 916; 436/1; 493/375, 961; 374/143, 162

[56] References Cited

U.S. PATENT DOCUMENTS

| | | | |
|---|---|---|---|
| 59,678 | 11/1866 | Storer | 40/665 |
| 417,358 | 12/1889 | Lea et al. | 292/307 A |
| 478,185 | 7/1892 | Barnum | 40/663 |
| 612,998 | 10/1898 | Thomas | 24/30.5 R |
| 847,295 | 3/1907 | Randall | 229/76 |
| 858,264 | 6/1907 | Daugherty | 292/307 A |
| 1,304,417 | 5/1919 | Underwood | 40/663 |
| 1,306,492 | 6/1919 | Lyons | 40/299 |
| 1,430,641 | 10/1922 | Ginn | 40/663 |
| 1,506,956 | 9/1924 | Thompson | 40/299 |
| 1,602,309 | 10/1926 | Martineau | 292/307 A |
| 1,799,701 | 12/1928 | Prudden | 292/307 A |
| 1,894,015 | 1/1933 | Bernstein | 374/143 |
| 2,016,059 | 10/1935 | Stevens | 229/74 |
| 2,440,666 | 4/1948 | Miller | 229/74 |
| 2,468,355 | 4/1949 | Ambler | 24/67 R |
| 3,034,819 | 5/1962 | Tupper | 292/307 R |
| 3,078,182 | 2/1963 | Crone, Jr. et al. | 436/1 |
| 3,197,830 | 8/1965 | Hoardley | 24/16 PB |
| 3,322,325 | 5/1967 | Bush | 24/30.5 P |
| 3,468,050 | 9/1969 | Pool | 40/302 |
| 3,568,627 | 3/1971 | Selinger | 422/57 X |
| 3,744,094 | 7/1973 | Bach | 24/30.5 X |
| 3,775,882 | 12/1973 | Wheeler | 40/645 |
| 3,834,824 | 9/1974 | Jahn | 24/16 PB |
| 3,924,800 | 12/1975 | Desmond et al. | 292/307 A |
| 3,994,085 | 11/1976 | Groselak et al. | 40/630 X |
| 4,194,622 | 3/1980 | Lewis | 422/119 X |
| 4,331,257 | 5/1982 | Taschner | 220/324 |
| 4,363,421 | 12/1982 | Shoemaker | 220/319 |
| 4,379,372 | 4/1983 | Alexander et al. | 40/645 |
| 4,454,956 | 6/1984 | Patterson | 220/214 |
| 4,460,119 | 7/1984 | Goodfellow et al. | 229/74 X |
| 4,509,196 | 4/1985 | Sak et al. | 206/813 X |
| 4,562,047 | 12/1985 | Sestak et al. | 422/300 |
| 4,570,368 | 2/1986 | Stover | 40/645 |
| 4,625,885 | 12/1986 | Nichols | 220/214 |
| 4,631,845 | 12/1986 | Samuel et al. | 40/638 |
| 4,709,396 | 11/1987 | Voshall et al. | 383/5 |
| 4,749,084 | 6/1988 | Pereyra | 206/459 |
| 4,783,321 | 11/1988 | Spence | 422/300 |
| 4,818,502 | 4/1989 | Taschner | 422/310 |
| 4,820,499 | 4/1989 | Taschner | 422/310 |
| 4,915,913 | 4/1990 | Williams et al. | 422/119 |
| 4,916,841 | 4/1990 | Dawson | 40/6 X |
| 4,921,277 | 5/1990 | McDonough | 283/900 X |
| 5,225,162 | 7/1993 | Scoville | 422/56 |

FOREIGN PATENT DOCUMENTS

| | | | |
|---|---|---|---|
| 3022318 | 12/1981 | Germany . | |
| 3116036 | 7/1984 | Germany . | |
| 3544341 | 6/1987 | Germany . | |
| 4022952 | 10/1991 | Germany . | |
| 503846 | 4/1939 | United Kingdom | 40/645 |

*Primary Examiner*—James C. Housel

*Assistant Examiner*—Arlen Soderquist

*Attorney, Agent, or Firm*—Harris Beach & Wilcox

[57] ABSTRACT

A locking device in the shape of a unitary body formed from a bio-degradable material which includes an element with at least one free end formed integral with said body. The severable element is designed to engage and secure a container lock mechanism when the container is in a closed position, whereby the free end of the element is capable of being mechanically or adhesively secured to said unitary body to form a seal, with said device being designed to fracture upon opening of the container lock mechanism thereby providing visible evidence of the lock mechanism being opened.

1 Claim, 3 Drawing Sheets

50 42 48 46 44 10 54 52

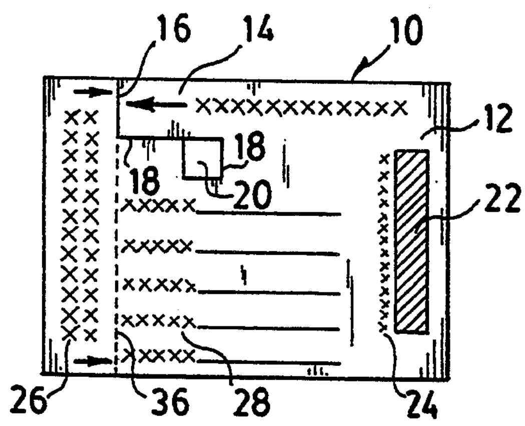
FIG. 1
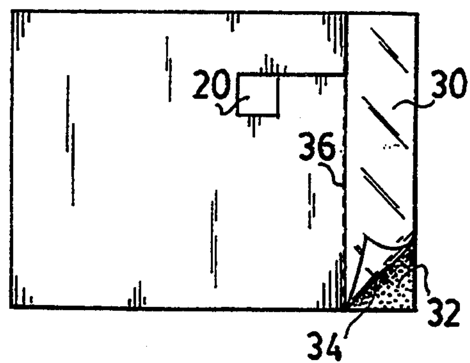
FIG. 2
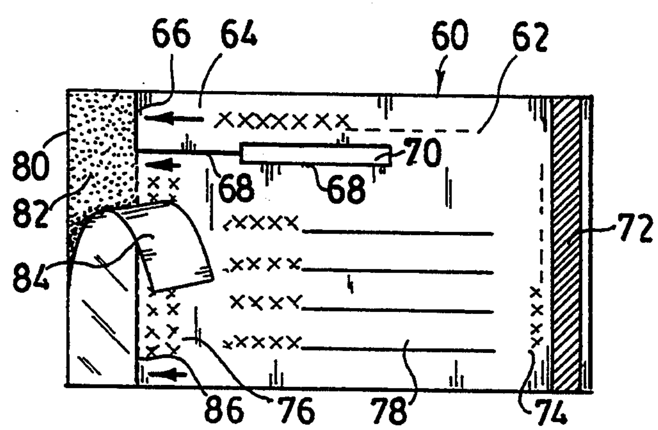
FIG. 5
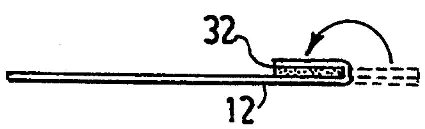
FIG. 3
FIG. 4
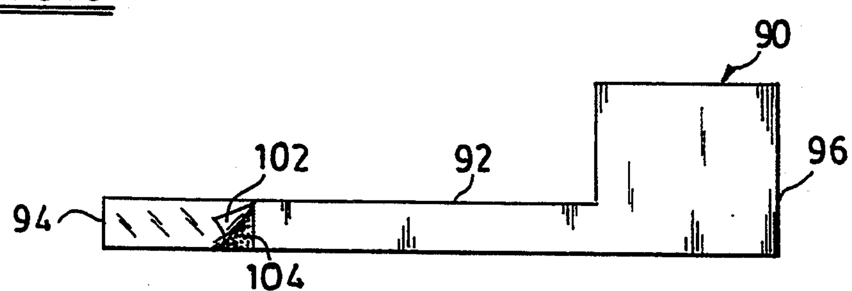
FIG. 6A
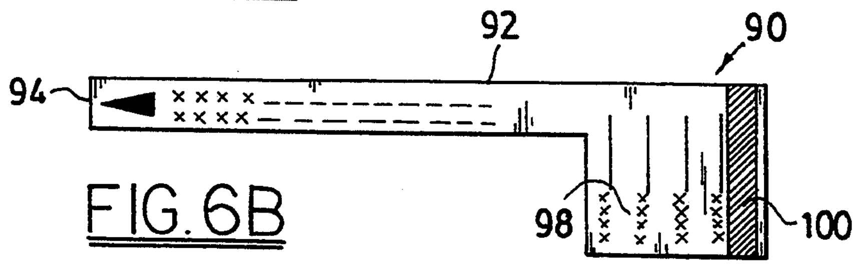
FIG. 6B

METHOD OF USING A DISPOSABLE TAMPER EVIDENT LOCKING DEVICE

This is a continuation of copending application(s) Ser. No. 07/598,946 filed on Oct. 17, 1990, now U.S. Pat. No. 5,225,162.

BACKGROUND OF THE INVENTION

1. Field of the Invention

The present invention relates in general to locking mechanisms for containers for sterilization and storing articles, and more particularly to a disposable tamper evident security device for providing an indication of whether the container has been opened subsequent to sterilization.

2. Description of the Prior Art

Sterilization container systems have been developed to facilitate the storage of sterilized articles in a manner such that their sterilized state is maintained during storage. These container systems permit entry of the sterilizing medium into the container during the performance of the sterilization process, but prevent the entry of contaminating organisms into the containers.

Sterilization containers which contain articles which have been sterilized are commonly left unattended for relatively long periods of time before the articles are used. During this storage period the possibility exists that the container will be opened, causing contamination of the articles, and then subsequently reclosed. Such an event is not readily visible. Most medical instrument sterilization containers employ some form of security device to give evidence of sterile integrity prior to use. Closures for sterilization containers are often provided with seals which must be destroyed to enable opening of the locking mechanism for the container. It is also known to use so-called indicator adhesive tapes as seals, i.e. tapes which change their color during sterilization. The locking mechanism of such sterilizing containers can only be opened by destroying such an indicator tape.

U.S. Pat. No. 4,820,499 describes a device and a means for securing a paper data card which also indicates by a punched hole that the sterilizing container has been opened. Devices described in U.S. Pat. Nos. 4,562,047 and 4,915,913 are fabricated of plastic and designed to be fractured when the container is opened and provide a permanent indication of the incident. These devices are also provided with means for indicating that the container has been exposed to a sterilization process.

All known "tamper evident" devices require additional elements to: (1) automatically indicate whether the container has been sterilized and (2) indicia fields for inscribing data. Many of the current "tamper evident" devices are fabricated of high temperature resistant injection moldable plastic resins. These resins are expensive and consume non-renewable resources (oil), are non-biodegradable and when incinerated, burn with high temperatures and emit toxic gases which are known to pollute the atmosphere.

An object of the present invention is to provide a "tamper evident" device which integrates the various discrete elements, i.e. locking function, sterilization indicator and data elements into a single disposable device.

Another object of the present invention is to provide a tamper evident locking device that reduces the impact on the waste disposal systems in health care facilities and land fills, while reducing or eliminating the production of toxic by-products resulting from incineration.

A further objective of the present invention is to provide an inexpensive disposable "tamper evident" locking device having simple, yet functionally effective design features.

SUMMARY OF THE INVENTION

The present invention is directed to a tamper evident seal or locking device for a sterilization container, and in one embodiment, comprises of a body formed of heavy paper or paperboard tag stock, a severable element with a free end which has been formed by appropriate die-cuts from said body, a field or area to which sterilization indicator material is applied, a second field or area printed with instruction for use indicia, a third field or area to which a permanent type pressure sensitive adhesive with release liner is applied, an area which has been die-cut and removed prior to use, and a crease to aid in folding the adhesive area to seal or lock the device.

In operation, the free end of the severable element is inserted into the bore or keyway of a closed latch mechanism of a sterilization container in such a way that the free end emerges from the open end and is free for attachment or locking. The pressure sensitive adhesive is "activated" by stripping away a protective release liner and the area containing the adhesive is folded along the crease to adhere to the free end of the severable element thereby completing the seal or locking action of the device. Upon opening the latch mechanism, the severable element is fractured, automatically indicating that the container has been previously opened.

BRIEF DESCRIPTION OF THE DRAWINGS

FIG. 1 is a plan view of the face side of one embodiment of a device of the present invention;

FIG. 2 is a view of the back side of the device of FIG. 1;

FIG. 3 is a side or edge view of the device of FIG. 1;

FIG. 4 is a view of the device of FIG. 3 with the device in the closed or locked position;

FIG. 5 is a plan view of the face side of a second embodiment of a device of the present invention.

FIG. 6A is a plan view of the backside an alternative embodiment of a device of the present invention;

FIG. 6B is a view of the front side of the device of FIG. 6*a;*

DETAILED DESCRIPTION OF THE INVENTION

Figure 6C:
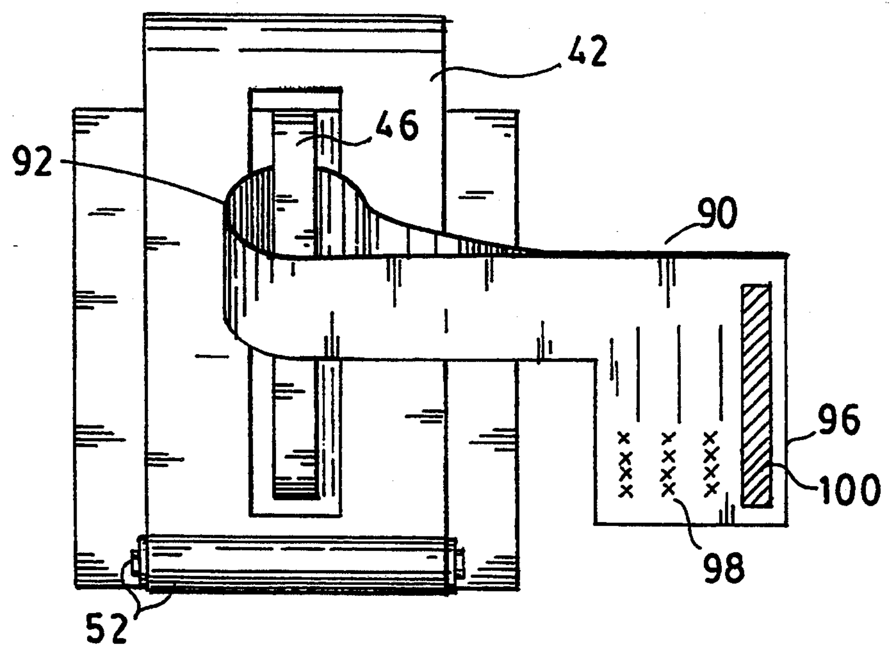
FIG. 6C is a perspective view showing the device of FIGS. 6A and 6B in the closed or locked position.

The locking device of the present invention, in its simplest embodiment, is in the shape of a unitary body formed from a biodegradable and renewable material, and includes a severable element with at least one free end formed integral with said unitary body. The severable element of the device is designed to engage a container lock mechanism and when in a locked or closed position the free end is mechanically or adhesively secured to said unitary body to form a seal, thus preventing its removal or opening of said lock mechanism without providing visible evidence of tampering.

FIG. 1 is a plan view of the face side of one embodiment of a tamper evident device 10 of the present invention. The device 10 has a body 12, a severable element 14 having a free end 16 which is formed by appropriate die-cuts 18, which also results in the formation of an opening or hole 20. Opening or hole 20 serves as a means of locating the device such that it prevents movement laterally when the device is in the locked or closed position. The device further contains a first field or area 22 to which is applied a sterilization indicator material, a second field 24 to which is printed sterilization indicator interpretation instructions, a third field 26 to which is printed instructions for use, a fourth field 28 to receive variable data, and a fifth field 30 located on the back or side opposite the face side (FIG. 2) to which is applied a permanent type pressure sensitive adhesive 32 (FIG. 3) an appropriate protective release liner 34, and a crease 36 to aid in folding the adhesive field 30 when locking or closing the device. FIG. 4 illustrates a side view of the device of FIG. 1 where the release liner 34 has been stripped away and the end section containing the adhesive folded along crease 36 to seal or lock the device.

Figure 7:
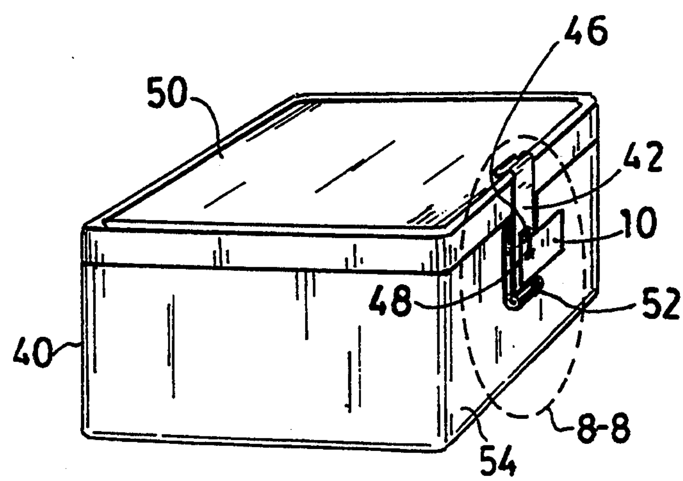
FIG. 7 is a perspective view of a sterilization container illustrating a lock mechanism utilizing the device of the present invention.
Figure 8:
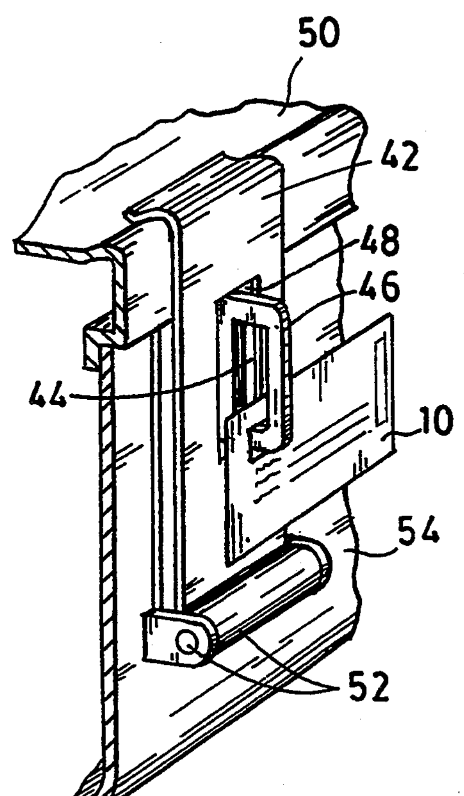
FIG. 8 is an enlarged view from FIG. 7 showing the latch mechanism in the closed position with the device of the present invention in the closed or locked position.

FIG. 7 illustrates a perspective view of a simplified version of a sterilization container 40 which incorporates a hasp type latching element 42 in a closed position such that a "D" shaped element 46 passes through the opening 48 in the hasp. Container 40 has a hinged cover 50 with the latching element 42 pivotably attached at 52 to the front 54 of the container. To lock the container, the free end of device 10 of FIG. 1 is inserted into the opening or keyway 44 in "D" shaped element 46. FIG. 8 is an enlarged view of area 8—8 of FIG. 7 and shows sterilization container 40 having hinged hasp type latching element 42 in the closed position. The free end 16 of severable element 14 is passed into and through opening or keyway 44 in "D" shaped element 46 in such a way that the free end emerges from the open end and "D" shaped element 46 becomes trapped in opening or hole 20 which serves as a means of locating the device and preventing lateral movement. Constraint of movement of device 10 is desirable to prevent slippage of the severable element 14 through latching element 42, and to prevent interference with other container elements such as movable handles. The protective adhesive release liner 34 has been removed exposing the pressure sensitive adhesive 32. The area to which the pressure sensitive adhesive is applied then is folded along crease 36 and adhered to the free end 16 of the severable element 14 and body 12 thereby completing the seal or locking action.

Although the device of the present invention has been illustrated as fracturing or breaking through a location described as a severable element, it should be understood that the device can be designed to fracture at any location predetermined or random. In this embodiment, upon opening the latch mechanism, the element with one free end that has been sealed or locked becomes fractured at any desired location which may be defined by perforations or along a predetermined fault line, automatically indicating that the container has been previously opened.

Figure 9:
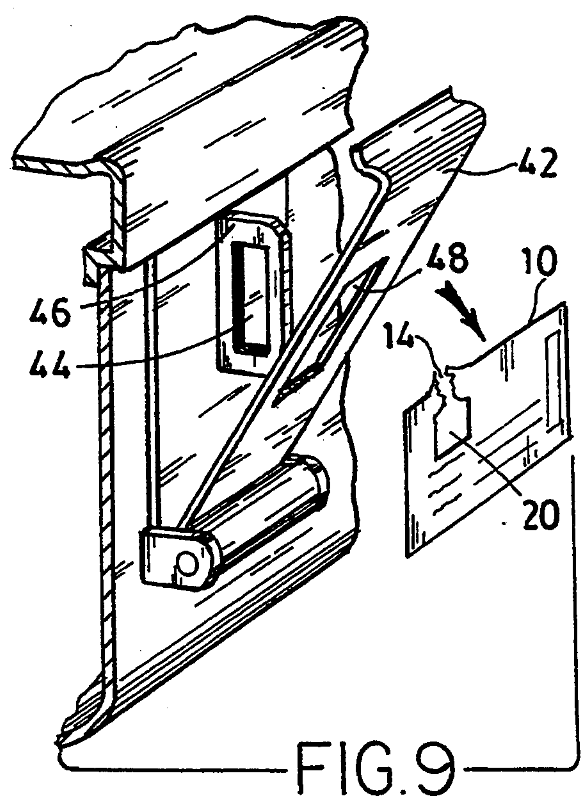
FIG. 9 is a view of the FIG. 8 with the latch mechanism in the open position.

FIG. 9 is an enlarged schematic illustration of the operation of a container latch mechanism of FIG. 8 showing the tamper evident device being severed as the "D" shaped element passes through the opening 48 in hinged hasp latch 42 as it travels to the open position. This movement of the hasp latch element 42 causes a shearing action with the "D" shaped element 46 thus fracturing or breaking severable element 14.

A second embodiment of the present invention is illustrated in FIG. 5, which is a plan view of the tamper evident device 60 which is substantially the equivalent of device 10 of FIG. 1. Device 60 has a body 62, a severable element 64 with one free end 66 which is formed by appropriate die-cuts 68 which also results in the formation of an opening or slot 70. Slot 70 serves as a means of locating the device and preventing lateral movement. Constraint of movement of the device is desirable to prevent slippage of the severable element 64 through the latching element 42 and to prevent interference with other container elements such as moveable handles. The device further contains a first field 72 to which is applied a sterilization indicator material, a second field 74 to which is printed sterilization indicator interpretation instruction indicia, a third field 76 to which is printed instructions for use, a fourth field 78 to receive variable data, and a fifth field 80 on the face side, to which is applied a permanent type pressure sensitive adhesive 82 and appropriate protective release liner 84, and a crease 86 to aid in folding. In this embodiment, the adhesive layer is contained on the same side as the various fields.

FIGS. 6A and 6B illustrate plan views of the back and front, respectively, of an alternative embodiment of the present invention. In this embodiment, device 90 contains a severable element which comprises an elongated strip section 92 having a free end 94 and an opposite end section 96 which contains the indicia 98 and indicator material 100.

Figure 6D:
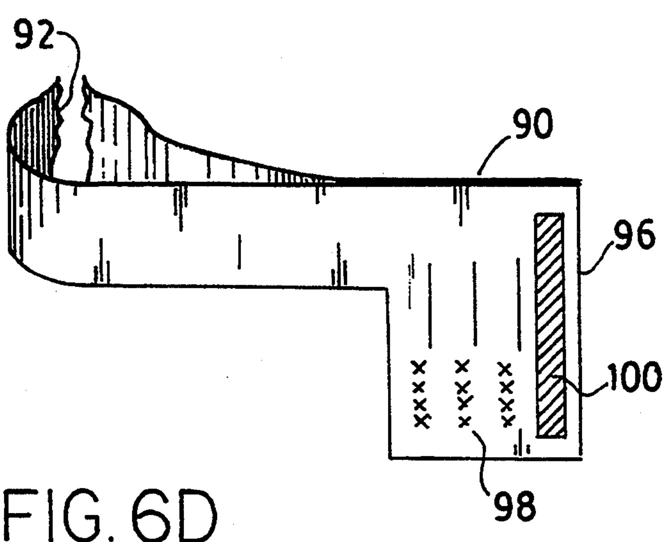
FIG. 6D is a view of the device of FIG. 6C, in the severed or fractured condition.

In operation the free end 94 of the severable element 92 of device 90 passes into and through the bore or opening of a keyway not unlike element 46 shown in FIG. 8. The protective release liner 102 is removed exposing the pressure sensitive adhesive area 104 on the back face of the said free end 94; the free end is passed around a protruding segment of said keyway and the adhesive side of the free end is secured to itself forming a loop as shown in FIG. 6C. FIG. 6D is a schematic illustration of the operation of a container latch mechanism of 6C showing the tamper evident device being severed as the latch mechanism 42 travels to the open position. The movement of the latch mechanism severs the severable element 92.

It should be understood that geometric configurations other than those illustrated by the drawings may also be used in making a device of the present invention. For example:

1. A device where an elongated severable element with one free end formed from a unitary body, said elongated severable element having a shaped end to engage a slot in said unitary body and become trapped. An alternative mechanical means for fastening could include the form of an embossed or raised surface designed to frictionally engage a hole or opening.
2. A device where an elongated severable element with one free end formed from a unitary body, said elongated severable element having a pressure sensitive adhesive area on the back face of said free end, and when said free end is engaged in a slot in said unitary body, and the adhesive area exposed and folded back and then adhered to said unitary body.

3. A device with an elongated severable element with two free ends with an adhesive area on the back face of the two free ends. A seal being made when the two adhesive areas are mated together. Indicia fields and sterilization indictor fields can be applied along the elongated element.

The body of the tamper evident device of the present invention is preferably made from paper tag stock, paperboard or other suitable biodegradable material. The preferred material is 12 point (0.012" caliper) paperboard tag stock. The caliper of tag stock was selected as being most compatible with available in-line printing and die-cutting equipment. Higher caliper material may be desirable in some applications but would most likely require an off-line secondary die-cutting operation. An acceptable caliper range for the paperboard tag stock being 12–24 point. The preferred material of heavy paper or paperboard may also consist of multiple layers of paper/paperboard laminated to achieve desired thickness and/or stiffness.

Other biodegradable materials that could be used to make the device of the present invention include wood, natural fabrics, composites of natural materials in a matrix of biodegradable and non-toxic binders, laminates of natural fabrics and wood.

A polymeric film could also be used but would deviate from the intended environmental solution to waste disposal and atmosphere pollution, unless one is found to be biodegradable and non-toxic.

The sterilization indicator ink in the preferred form and commercially available under trade designation G/S FWC-428C from Tempil Incorp, N.J. The composition may be flexographically printed at any appropriate location. The sterilization indicator ink being reactive to both steam or ethylene oxide gas sterilization processes with the ink changing a distinctive and different color under each sterilization condition. Without deviating from the intended purpose, one or more sterilization indicator ink formulations may be applied, each designed to react to a different sterilization process condition with a distinctive and different color change for each process condition.

The permanent type pressure sensitive adhesive in the form of a double-side adhesive laminate such as Adhesives Research, Inc., grade DEV 7427 CO 6504D or equivalent may be used. Pressure sensitive adhesive may be directly applied to the paperboard as a discrete adhesive element and a release liner applied as a secondary operation.

Although the invention is illustrated and described in relationship to specific embodiments, it is nevertheless not intended to be limited to the details shown, since various modifications and structural changes may be made without departing from the spirit of the invention.

What is claimed is:

1. A method for securing a lock mechanism of a sterilization container to provide evidence of the mechanism being opened which comprises:

(a) providing a locking device for engaging and securing a container lock mechanism which contains a closure means, said device comprising a unitary body made from biodegradable material having a sterilization indicator means contained thereon, said unitary body having a planar configuration which includes an element with at least one free end, said element being formed integral with the said unitary body by appropriate die cuts which result in the formation of an opening or hole within said unitary body, said hole or opening functioning as a means for locating the device on the closure means of said lock mechanism, and means to secure the free end of said element to said unitary body to form a seal, wherein said element fractures upon opening of said container lock mechanism, thereby providing visible evidence of the lock mechanism being opened;

(b) inserting said free end of the device through the closure means of a lock mechanism such that said closure means extends through said opening; and (c) securing the lock mechanism of the container by mechanically or adhesively contacting said element to said unitary body to form a seal which upon opening of the container lock mechanism said element fractures and provides visible evidence of the lock mechanism having been opened.

* * * * *